United States Patent
Mamigonians et al.

(10) Patent No.: US 11,622,704 B2
(45) Date of Patent: Apr. 11, 2023

(54) PRESSURE-COMPENSATING NON-INVASIVE BLOOD-COMPONENT MEASUREMENT

(71) Applicant: Zedsen Limited, London (GB)

(72) Inventors: Hrand Mami Mamigonians, London (GB); Aslam Sulaimalebbe, Cardiff (GB); Armen Mamigonians, London (GB); Anastasios Kanakis, Cambridge (GB); Daniel Ioan Polec, London (GB); Vivekram Sivasailam, West Drayton (GB)

(73) Assignee: Zedsen Limited, London (GB)

( * ) Notice: Subject to any disclaimer, the term of this patent is extended or adjusted under 35 U.S.C. 154(b) by 592 days.

(21) Appl. No.: 16/859,289

(22) Filed: Apr. 27, 2020

(65) Prior Publication Data

US 2020/0337613 A1 Oct. 29, 2020

(30) Foreign Application Priority Data

Apr. 27, 2019 (GB) ..................................... 1905972

(51) Int. Cl.
*A61B 5/145* (2006.01)
*A61B 5/00* (2006.01)
*A61B 5/0531* (2021.01)

(52) U.S. Cl.
CPC ........ *A61B 5/14532* (2013.01); *A61B 5/0531* (2013.01); *A61B 5/6826* (2013.01);
(Continued)

(58) Field of Classification Search
CPC .... G06F 3/0443; G06F 3/0445; G06F 3/0446;
A61B 5/053–0531; A61B 5/0533; A61B 5/0537; A61B 5/26; A61B 5/277–279; A61B 5/14532; A61B 5/1477; A61B 5/4869; A61B 5/4881; A61B 5/6826; A61B 5/6843; A61B 5/6897–6898; A61B 2090/065; A61B 2562/0214; A61B 2562/043–046; A61B 5/05; A61B 5/14546; A61B 2562/0209;
(Continued)

(56) References Cited

U.S. PATENT DOCUMENTS 8,994,383 B2 3/2015 Mamigonians
2002/0026123 A1* 2/2002 Pearlman ........... A61B 17/3403
600/547

(Continued)

*Primary Examiner* — Navin Natnithithadha
*Assistant Examiner* — Alice Ling Zou
(74) *Attorney, Agent, or Firm* — Cooper Legal Group, LLC

(57) ABSTRACT

A pressure compensating non-invasive blood-component measuring device has electrically insulated parallel electrodes mounted on a dielectric membrane (106). A main circuit board (201) provides electrical connections to the electrodes and has an orifice (402) to allow flexing. A housing supports the main circuit board, with a second orifice to facilitate the application of a finger onto the insulated electrodes. A bottom circuit board (401) supports a force sensor (408) and fixing elements (313, 314) secure the bottom circuit board to the top circuit board, such that the bottom circuit board does not contact the housing directly. An intermediate board (316) is guided but not restrained by the fixing elements, and is arranged to apply force onto said force sensor.

15 Claims, 9 Drawing Sheets

(52) U.S. Cl.
CPC ............ *A61B 5/6843* (2013.01); *A61B 5/742* (2013.01); *A61B 5/0048* (2013.01); *A61B 2562/02* (2013.01); *A61B 2562/0209* (2013.01); *A61B 2562/0214* (2013.01); *A61B 2562/16* (2013.01)

(58) Field of Classification Search
CPC ......... A61B 2562/0247; A61B 2562/164–166; A61B 5/02–0295
See application file for complete search history.

(56) References Cited

U.S. PATENT DOCUMENTS

| | | | |
|---|---|---|---|
| 2008/0228050 A1* | 9/2008 | Hwang | A61B 5/14535 600/316 |
| 2009/0312615 A1* | 12/2009 | Caduff | A61B 5/0531 600/347 |
| 2014/0228654 A1* | 8/2014 | Kim | A61B 5/14532 600/561 |
| 2017/0086686 A1* | 3/2017 | Narasimhan | A61B 5/02141 |
| 2017/0319146 A1* | 11/2017 | Park | A61B 5/02255 |
| 2018/0177413 A1* | 6/2018 | Kwon | A61B 5/6898 |

* cited by examiner

PRESSURE-COMPENSATING NON-INVASIVE BLOOD-COMPONENT MEASUREMENT

CROSS REFERENCE TO RELATED APPLICATIONS

This application claims priority from United Kingdom Patent Application number 1905972.4, filed on Apr. 27, 2019, the whole contents of which are incorporated herein by reference.

BACKGROUND OF THE INVENTION

The present invention relates to a pressure-compensating non-invasive blood-component measuring apparatus. The present invention also relates to a method of measuring applied pressure, when a finger is pressed against a non-invasive blood-component detector.

It is known to deploy electric fields between capacitively coupled electrodes in an attempt to determine permittivity characteristics, in the hope of obtaining an indication of blood glucose levels. It is also known to compensate these measurements with respect to temperature. However, further research conducted by the inventor has shown that glucose measurements are also influenced by applied pressure, particularly when glucose is being monitored within the capillaries of a fingertip. Thus, an accurate measurement of applied pressure is required to achieve a practical level of compensation. Furthermore, the pressure measurement should be with respect to the pressure of the finger upon the electrode membrane and should not be influenced by other forces, possibly as a result of pressure being applied to other regions of a housing.

BRIEF SUMMARY OF THE INVENTION

According to a first aspect of the present invention, there is provided a pressure compensating non-invasive blood-component measuring apparatus, comprising: a plurality of electrically insulated substantially parallel electrodes mounted on a dielectric membrane; a main circuit board providing electrical connections to said electrodes, having a first orifice below said electrodes to allow flexing of said dielectric membrane; a housing for supporting said main circuit board, with a second orifice to facilitate the application of a finger onto said insulated electrodes; a bottom circuit board supporting a force sensor; plural fixing elements securing said bottom circuit board to said top circuit board, such that said bottom circuit board does not contact said housing directly; and an intermediate board that is guided but not restrained by said fixing elements, wherein said intermediate board is arranged to apply force onto said force sensor.

In an embodiment, the plural fixing elements are metal rods, each having an upper end and a lower end; said upper ends are secured to said main circuit board; and said lower ends are secured to said bottom circuit board. However, other materials could be used for the rods and alternative types of fixing could be adopted.

In an embodiment, the intermediate board includes an electrically conductive ground plane. This is advantageous if shielding from electrical noise is required but may not be necessary in some applications.

An embodiment provides a plastic support located between the dielectric membrane and said intermediate board. Some embodiments may not require this support and when provided, alternative materials may be deployed.

In an embodiment, an extending portion of the force sensor extends above a top surface of said bottom circuit board. However, alternative configurations are possible to obtain the required result.

In an embodiment, the extending portion includes a metal ball; and the metal ball contacts said intermediate board. The metal ball may be stainless steel but other materials and shapes could be used for the extending portion.

In an embodiment, the extending portion is surrounded by an elastomeric material and the elastomeric material contacts the intermediate board. The elastomeric material may be a silicone rubber with a Shore durometer (type A) of less than forty. However, other procedures may be adopted for returning the apparatus back to an original state prior to performing a further test.

In an embodiment, the main circuit board supports control electronics for energizing and monitoring the electrodes to produce output data and the operation of the control electronics is adjusted in response to pressure applied by the finger, as detected by said force sensor. Alternatively, the control electronics can be mounted elsewhere of communication can occur with external systems. In an embodiment, data is derived by permittivity measures made via capacitive coupling between electrodes, as described in U.S. Pat. No. 8,994,383.

In an embodiment, the main circuit board supports a visual display unit and the visual display unit is activated by the control electronics. The visual display unit is used to convey information to a user but alternative indicators could be adopted.

According to a second aspect of the present invention, there is provided a method of measuring applied pressure, when a finger is pressed against a non-invasive blood-component detector, comprising the step of: engaging a finger against substantially parallel electrically insulated electrodes, wherein said electrodes are supported by a main circuit board with a first orifice and are exposed through a second orifice in a housing; energizing and monitoring selected electrodes to produce output data; and monitoring applied pressure by means of a force sensor supported by a bottom circuit board, wherein a plurality of fixing elements rigidly secure said bottom circuit board to said top circuit board, an intermediate board contacts said force sensor, and said intermediate board and is guided but not restrained by said fixing elements.

In an embodiment, the method further comprises the steps of expanding an elastomeric material to return the intermediate circuit board to an original position, after being displaced by an application of pressure. However, alternative systems may be adopted to achieve this effect.

In an embodiment, the method further comprises the step of measuring the resistance of the force sensor to determine applied force, wherein increased applied force results in a higher measurable resistance. It should also be understood that reference may be made to applied pressure. Furthermore, alternative transducers may present changes in other attributes when force or pressure is applied.

Embodiments of the invention will be described, by way of example only, with reference to the accompanying drawings. The detailed embodiments show the best mode known to the inventor and provide support for the invention as claimed. However, they are only exemplary and should not be used to interpret or limit the scope of the claims. Their purpose is to provide a teaching to those skilled in the art.

Components and processes distinguished by ordinal phrases such as "first" and "second" do not necessarily define an order or ranking of any sort.

DETAILED DESCRIPTION OF EMBODIMENTS OF THE INVENTION

FIG. 1

Figure 1:
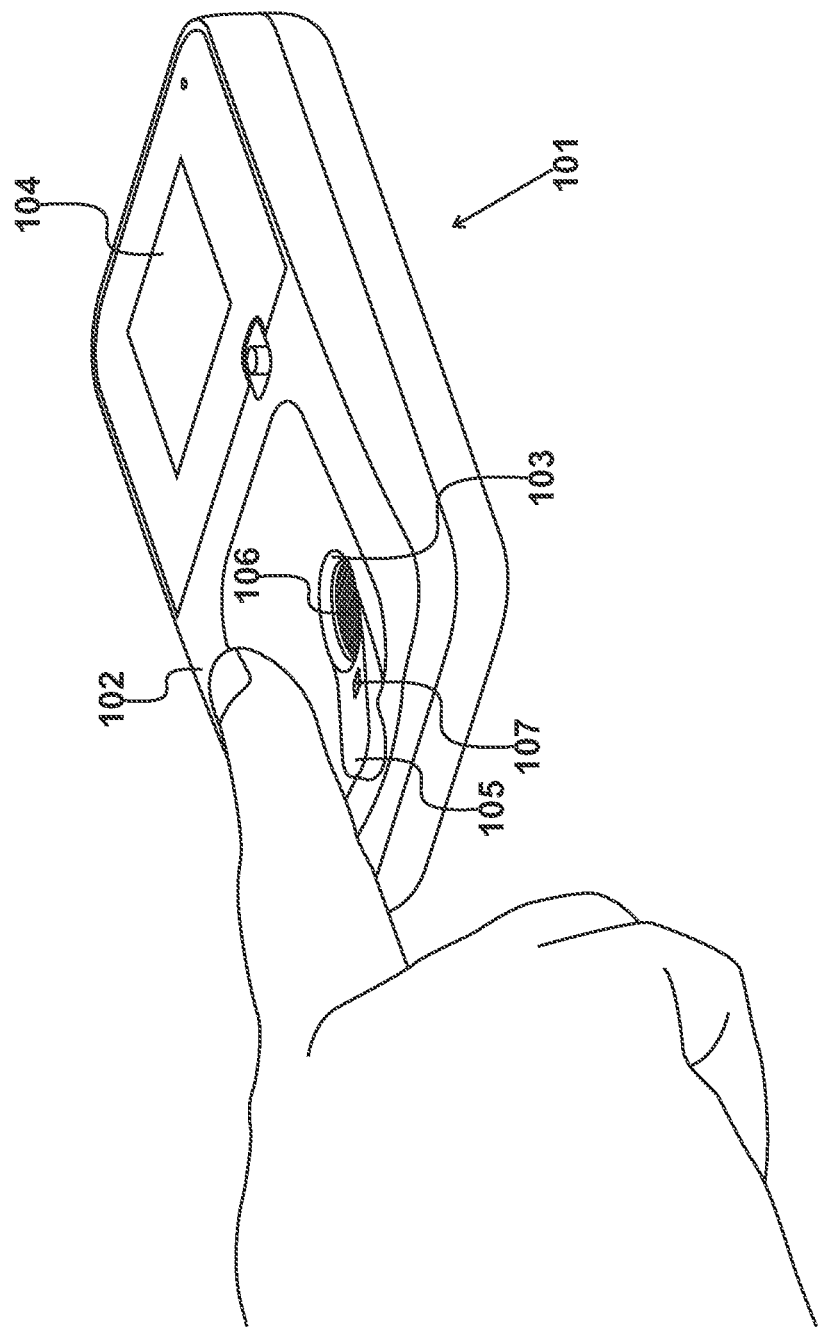
FIG. 1 shows a pressure-compensating non-invasive blood-component measuring apparatus.

A pressure-compensating non-invasive glucose blood-component measuring apparatus 101 is shown in FIG. 1. The apparatus has a plastic housing 102, with a membrane-exposing orifice 103. The housing also includes a visual display orifice 104 which, in this embodiment, is covered by a transparent cover, thereby allowing a visual display unit, supported by a main circuit board, to be seen during the operation of the apparatus.

A guide portion 105 guides a subject's finger into position, to contact with an electrode supporting membrane 106. The guide portion 105 also includes a temperature sensor 107. The electrodes are coated with a thin layer of an insulating material, such that an applied finger does not make electrical contact with the electrodes but does capacitively engage with the electrodes, such that it is possible for electric fields to enter the fingertip without an airgap being present.

FIG. 2

Figure 2:
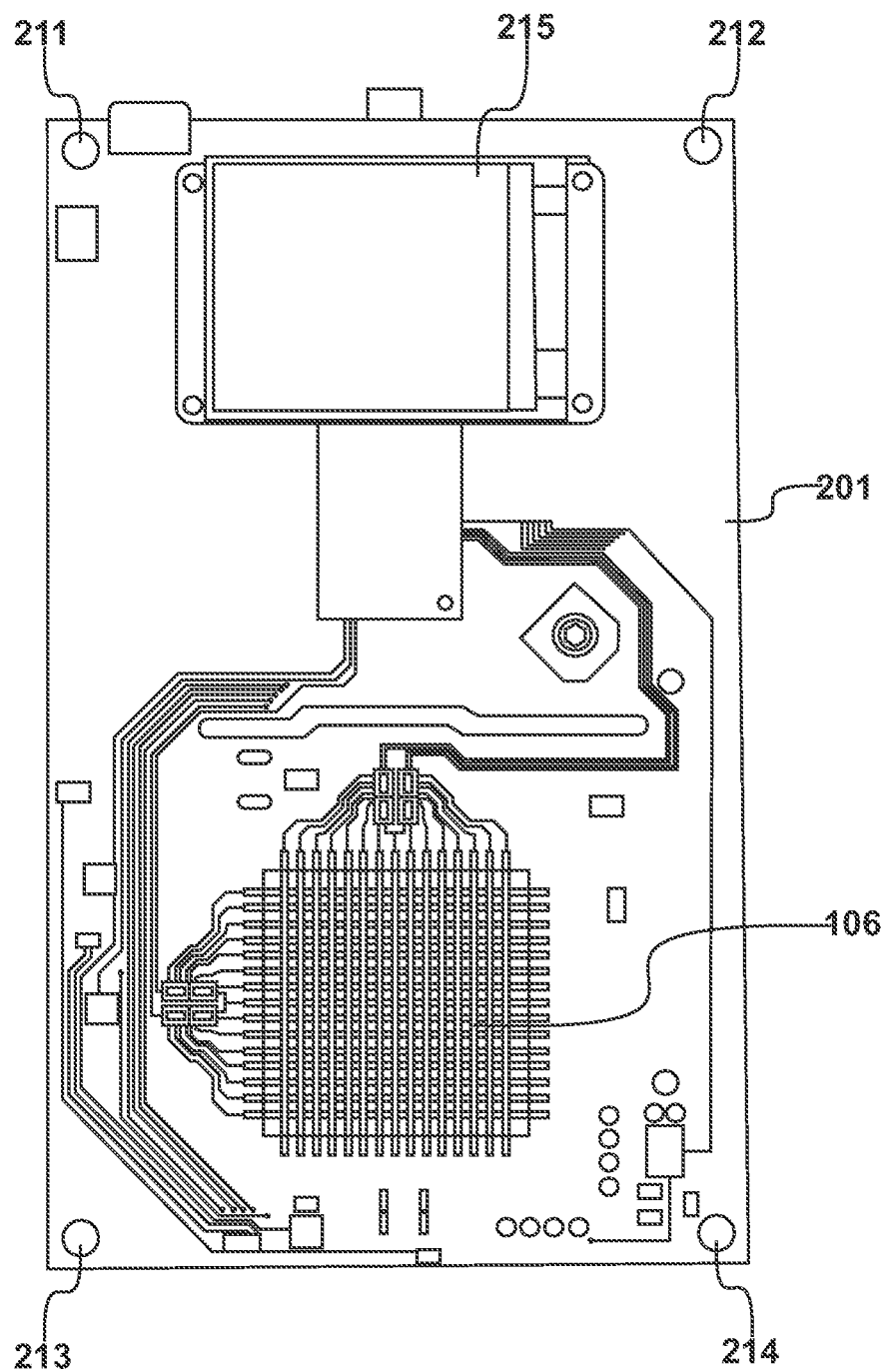
FIG. 2 shows a main circuit board of the apparatus of FIG. 1.

A main circuit board 201 is shown in FIG. 2, upon which the electrode supporting membrane 106 is itself supported above a first orifice. In this way, when pressure is applied to the membrane 106, a limited degree of movement is possible, resulting in force being applied to a force sensor, as described in detail with reference to FIG. 4 and FIG. 5.

A plurality of electrically insulated substantially parallel electrodes are mounted on the dielectric membrane 106 and the main circuit board 201 provides electrical connections to these electrodes. In this embodiment, in addition to a first set of substantially parallel electrodes mounted on the top surface of the dielectric membrane, a second set of substantially parallel electrodes are mounted on the underside of the dielectric membrane 106. As shown in FIG. 2, the first set of electrodes are mutually orthogonal to the second set of electrodes. In this way, it is possible for a first layering operation to be performed with respect to the first set, followed by a second layering operation being performed using the second set. Conventional position detection is also possible by sequentially energizing electrodes of one of these sets while monitoring selected electrodes of the second set.

Circuit board 201 is secured to the housing 102 at a first securing location 211, a second securing location 212, a third securing location 213 and a fourth securing location 214. A visual display unit 215 is attached to the main circuit board 201.

FIG. 3

Figure 3:
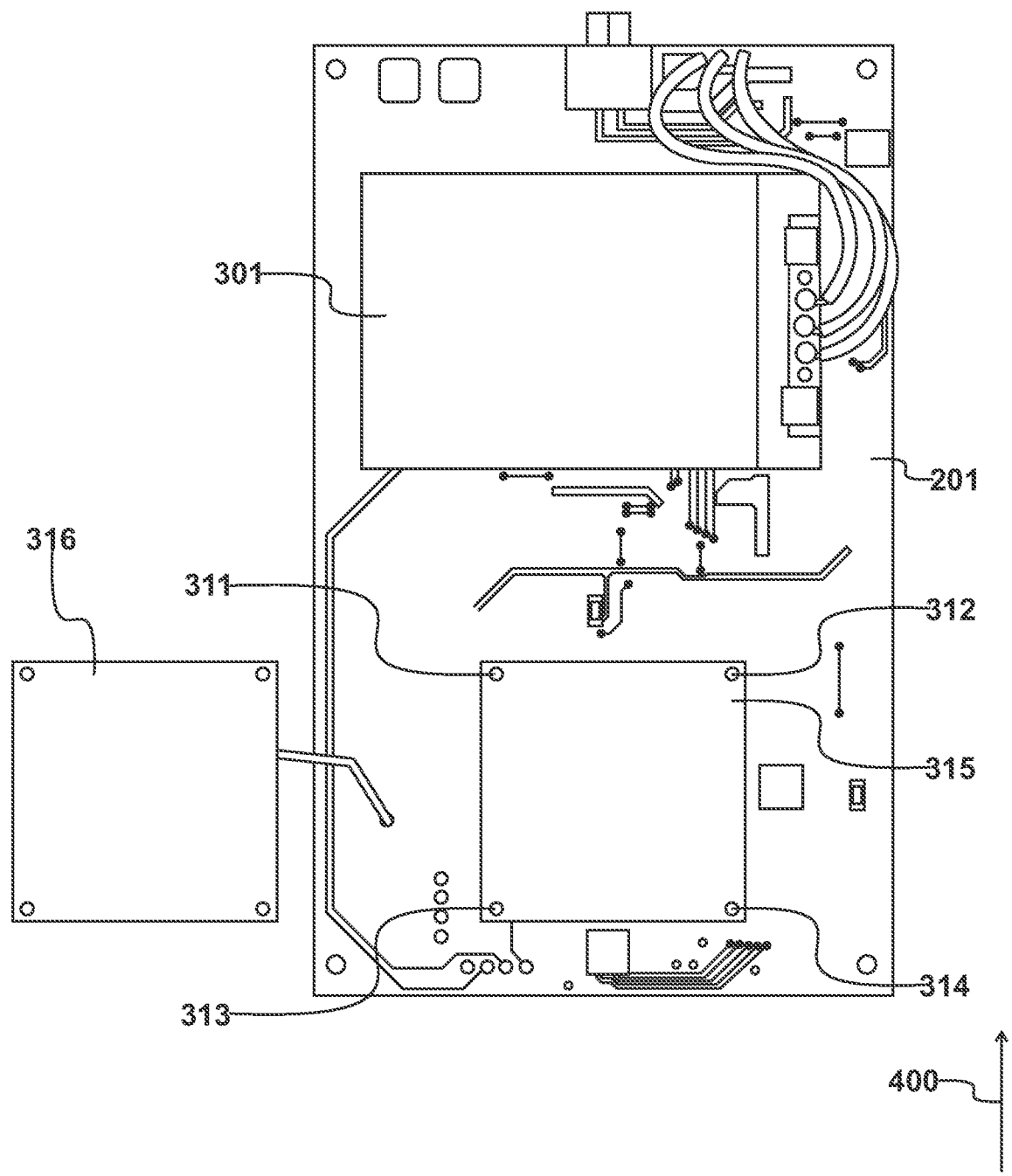
FIG. 3 shows the underside of the main circuit board identified in FIG. 2.

The underside of the main circuit board 201 is shown in FIG. 3. A rechargeable battery 301 provides electrical power for components within the apparatus. Plural fixing elements, consisting of a first rod 311, a second rod 312, a third rod 313 and a fourth rod 314 are secured to the main circuit board 201. In an embodiment, these fixing elements (rods) are secured by being soldered to circuit board 201. In an embodiment, a plastic support 315 is located on rods 311 to 314 to support the dielectric membrane 106. In an embodiment, the plastic support is derived from an acetyl material, selected such that electrical properties of this material do not change with respect to changes in temperature and humidity experienced within the operational environment.

Following the application of support 315, an intermediate board 316 is deployed over the rods 311 to 314, such that it is guided but not restrained by these fixing elements. In this way, board 316 is allowed to move and as such applies force onto the force sensor. In an embodiment, the intermediate board 316 includes an electrically conductive ground plane to provide electrical shielding to the lower side of the membrane 106.

After deploying the intermediate board 316, a bottom circuit board is located on the fixing elements 311 to 314 and thereafter secured to the fixing elements. Thus, the plural fixing elements secure the bottom circuit board to the top circuit board, such that the bottom circuit board does not move with respect to the main circuit board and the bottom circuit board does not contact the housing 102 directly.

Figure 4:
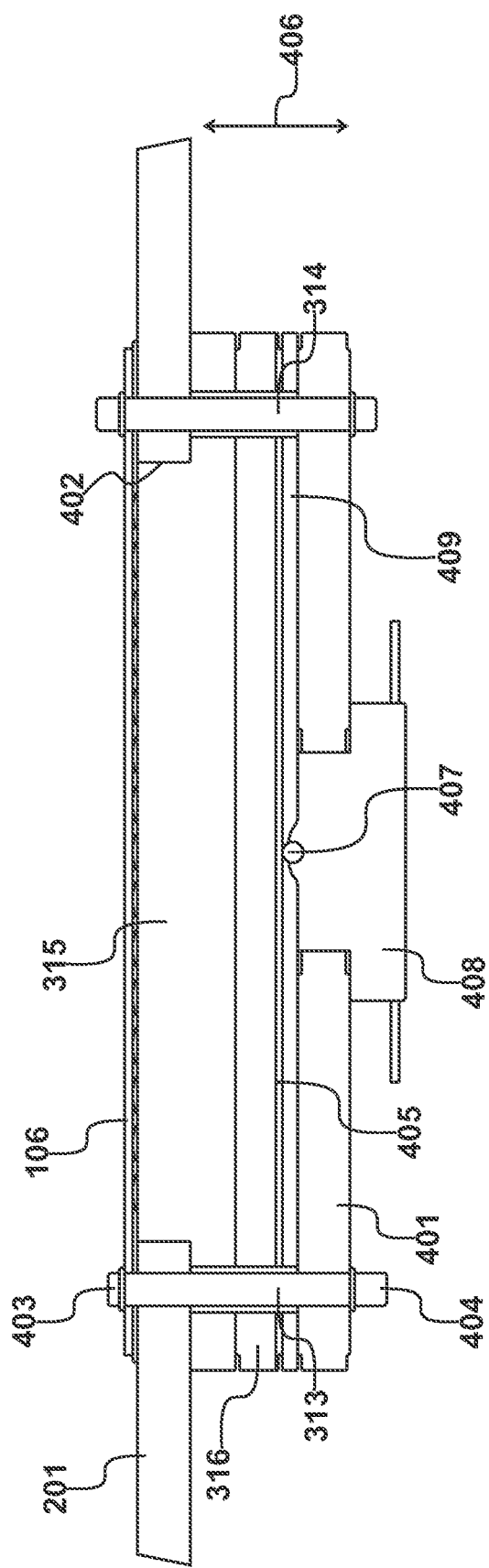
FIG. 4 shows a cross section of the apparatus of FIG. 1.

A cross-sectional view of the apparatus, looking in the direction of arrow 400, is shown in FIG. 4.

FIG. 4

Metal rod 313 and metal rod 314 are shown in the cross section of FIG. 4. These, along with the other two fixing rods, secure a bottom circuit board 401 to the top circuit board 201. The top circuit board 201 includes a first orifice 402 and the dielectric membrane 106 is supported over this orifice. In an embodiment, the membrane has a thickness of typically zero point one (0.1) millimetres and the main circuit board 201 has a typical thickness of one point six (1.6) millimetres. Each of the metal rods, including metal rod 313, has an upper end 403 and a lower end 404 such that, in an embodiment, the upper ends 403 are soldered to the main circuit board 201 and the lower ends 404 are soldered to the bottom circuit board 401.

The acetyl support 315 is shown in FIG. 4, along with the intermediate board 316 with a ground plane 405. Support 315 and board 316 are guided by the fixing elements 311 to 314 but are not restrained by these fixing elements, such that they are free to move in a vertical direction, as indicated by arrow 406. Relatively little movement may occur, typically up to a maximum of ten (10) micrometres, and it is unlikely that this would be perceived by a user. Movement is restrained by a metal ball 407 extending from a force sensor 408, wherein the metal ball 407 is in contact with the ground plane 405 attached intermediate board 316.

In this embodiment, the force sensor 408 is received within an orifice provided within the bottom circuit board 401, with the metal ball 407 extending above the plane of the bottom circuit board 401. Thus, in this way, an extending portion of the force sensor extends above a top surface of the bottom circuit board.

In an embodiment, the extending portion is surrounded by an elastomeric material 409. In an embodiment, the elastomeric material is a silicone rubber with a Shore durometer (type A) of less than forty. Thus, when flexing occurs, due to applied pressure, the elastomeric material 409 compresses. Thereafter, when force is removed, the elastomeric material will expand back to its original position, thereby ensuring that the apparatus is returned to a fully operational state.

Thus, in an embodiment, a subassembly is formed consisting of the bottom circuit board 401, and an inserted force sensor 408 with an extending portion surrounded by the elastomeric material 409. This subassembly is then located over the fixing elements and soldered into position.

FIG. 5

Figure 5:
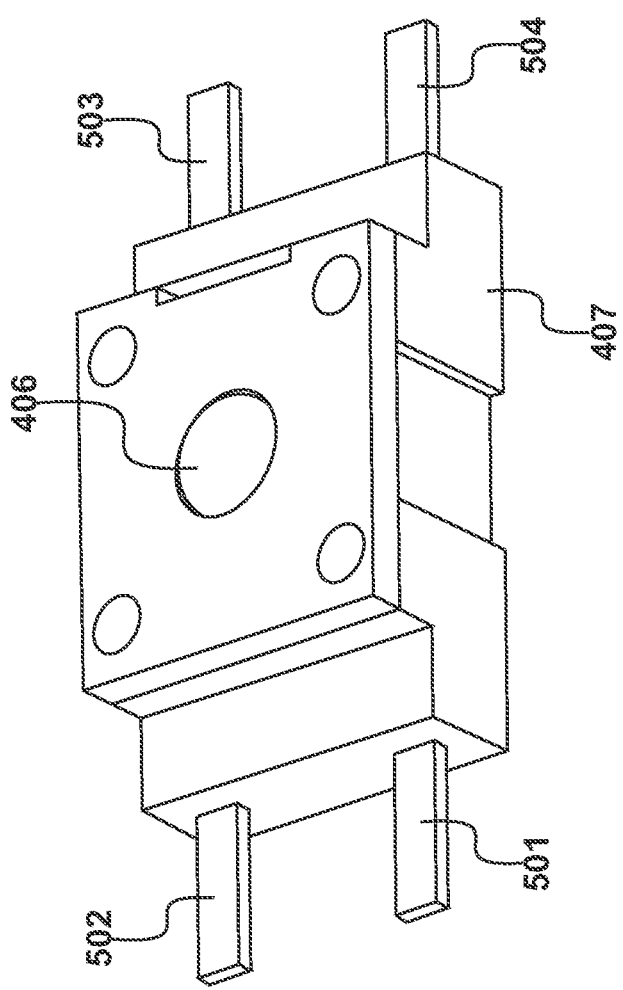
FIG. 5 details a force sensor of the type shown in FIG. 4.

An example of force sensor 408 is illustrated in FIG. 5, that may be an FSS low profile force sensor produced by Honeywell Corporation of 11 West Spring Street, Freeport, Ill. USA. As illustrated in FIG. 5, the metal ball (of stainless steel) is located at the centre of the sensor. Internally, the sensor uses a piezo-resistive micro-machined silicone sensing element. The sensor is configured such that its resistance will increase when the sensing element flexes under an applied force. The stainless-steel ball 406 concentrates this force directly onto the silicon sensing element. Thus, resistance changes in proportion to the amount of force being applied.

The device presents a first pin 501, a second pin 502, a third pin 503 and a fourth pin 504. Up to a maximum of twelve volts is applied across the first pin 501 and the third pin 503. Sensor output is then measured as a differential voltage across the second pin 502 and the fourth pin 504.

FIG. 6

The apparatus described with reference to FIG. 1 to FIG. 5 may be deployed when conducting a method of measuring applied pressure, when a finger is pressed against the non-invasive blood-component detector. Operation of the detector will be described, in this embodiment, with reference to the measurement of glucose levels in the blood, by way of illustration. However, it should be appreciated that a similar approach may be taken for measuring other blood components. These may include bio-chemical components, other organic components and inorganic components.

After performing a calibration procedure, the visual display unit 215 displays a message, along with a graphic, inviting a finger to be placed on the detector. Thus, instructions are displayed to a subject on the visual display unit, to assist the subject completing the overall monitoring procedure.

FIG. 7

Figure 6:
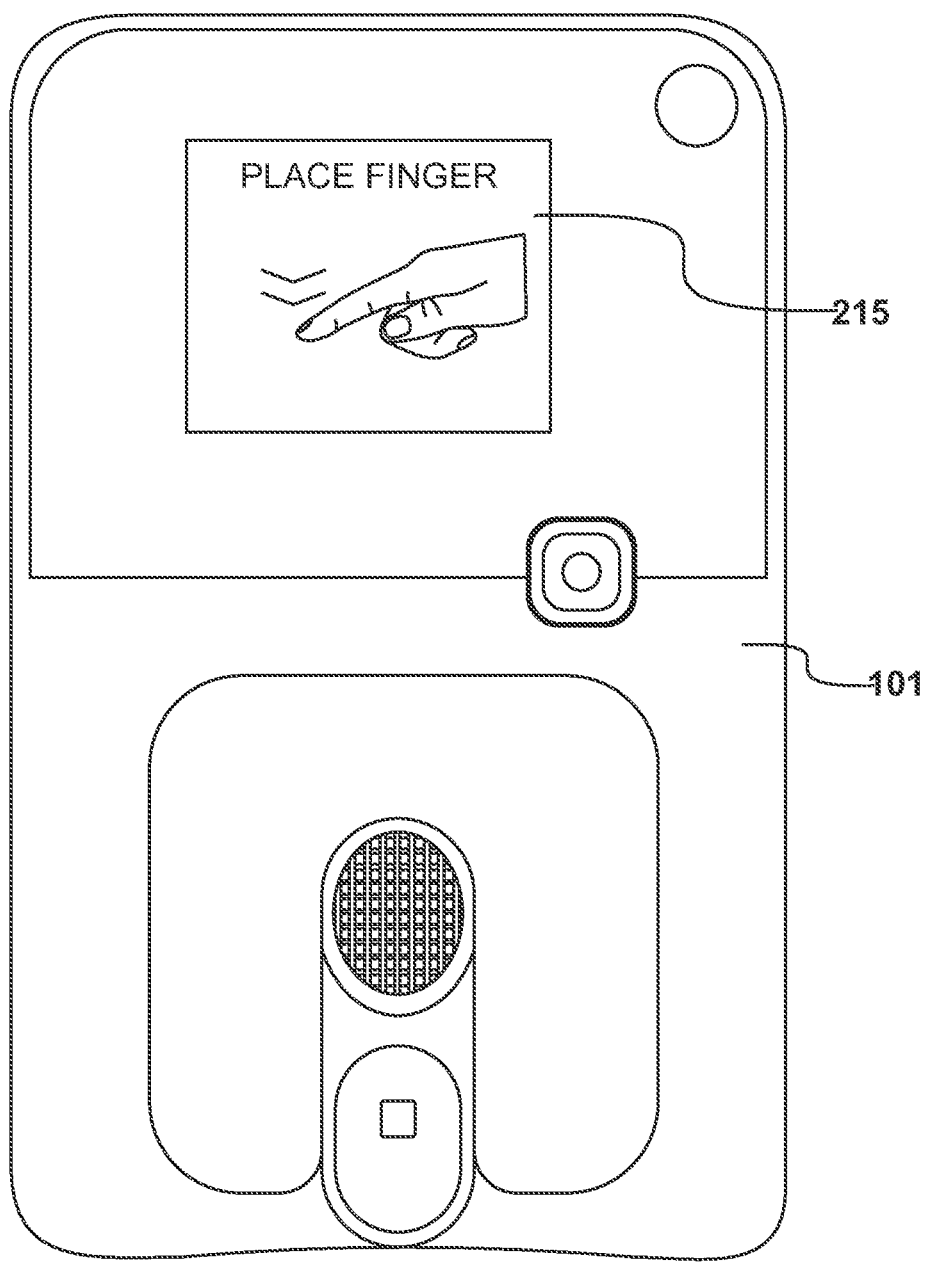
FIG. 6 shows a first stage of operation, inviting a finger to be placed on the apparatus.
Figure 7:
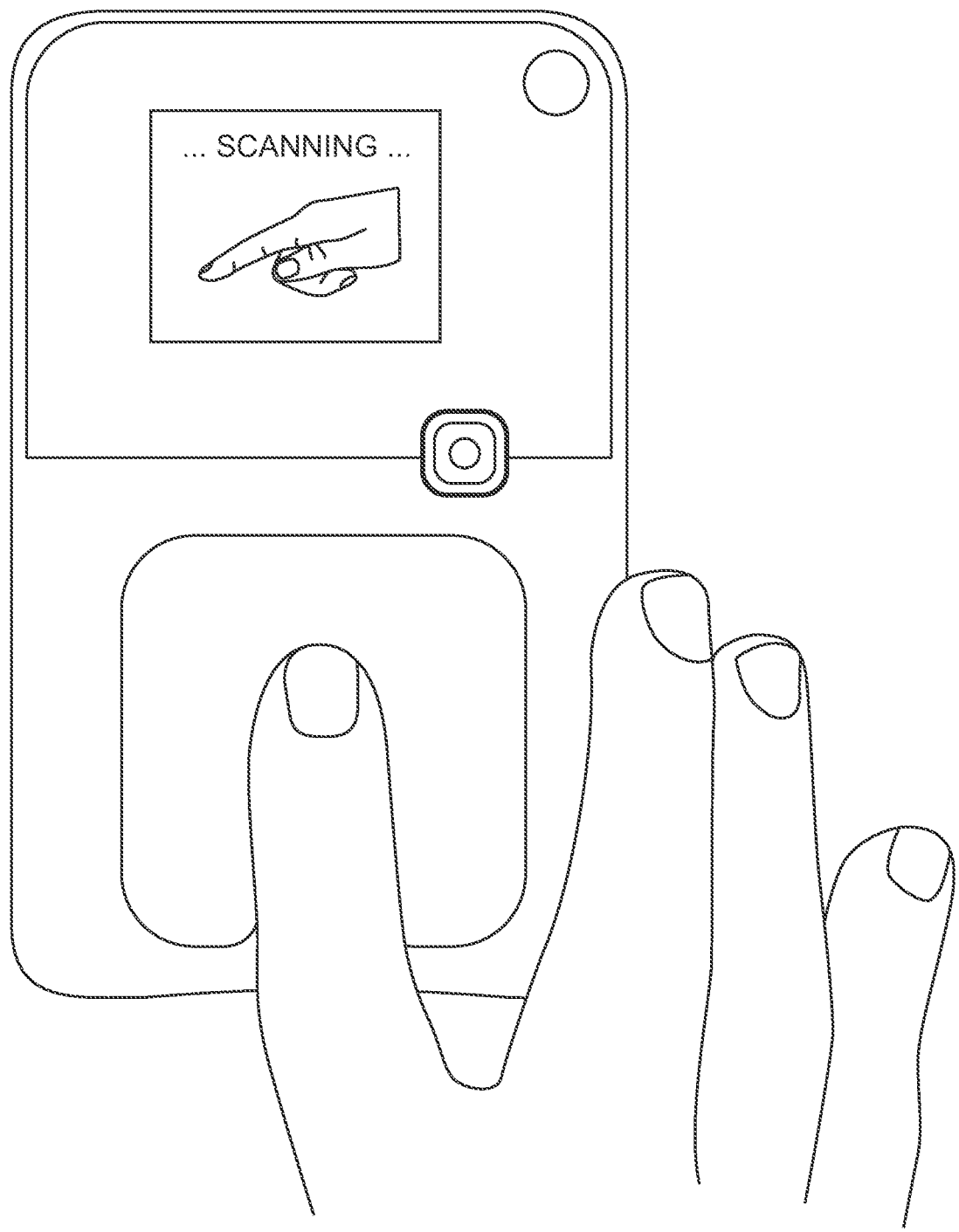
FIG. 7 shows a second stage of operation, confirming that a scanning operation is taking place.

After having been invited to deploy a finger, as described with reference to FIG. 6, a finger is engaged against the substantially parallel electrodes protected by the insulating coating. Thus, the electrodes are supported by the main circuit board and are exposed through the first membrane-exposing orifice in the housing.

A control circuit energizes and monitors selected electrodes to produce output data indicative of blood glucose concentrations. The visual display unit confirms this operation by identifying the apparatus as "scanning". Furthermore, throughout this procedure, the applied pressure is monitored by means of the force sensor supported by the bottom circuit board, wherein the fixing elements rigidly secure the bottom circuit board to the top circuit board, while the second intermediate circuit board includes a ground plane that is in contact with the first intermediate circuit board and the force sensor. As previously described, the intermediate circuit board and the plastic support are guided but not restrained by the fixing elements.

It is possible for varying degrees of pressure to be applied while the scanning procedure takes place. A small degree of movement occurs, up to fifty micrometres, but it is unlikely that a user would perceive this movement. Movement results in the compression of the (silicone rubber) elastomeric material.

FIG. 8

Figure 8:
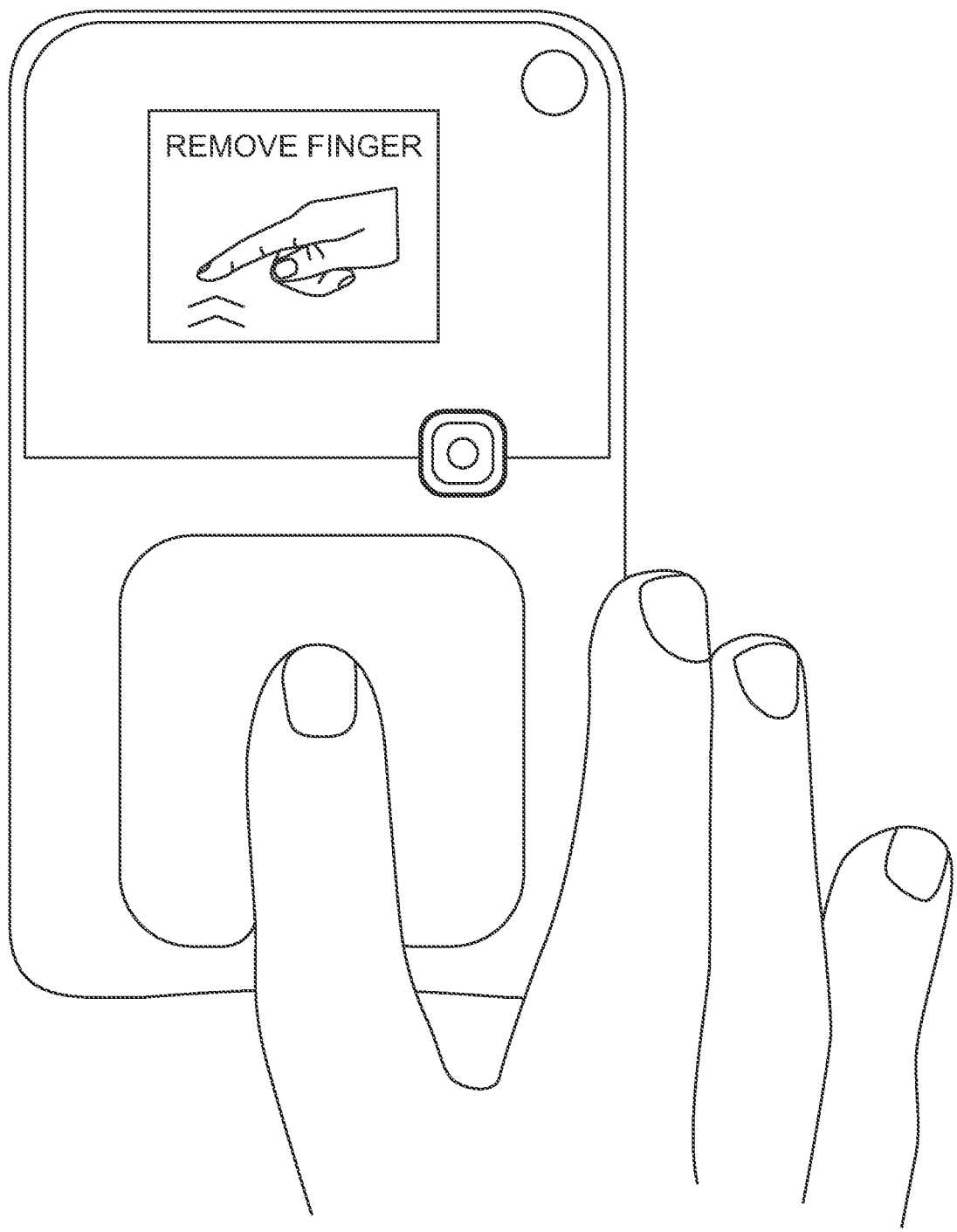
FIG. 8 shows a third stage of operation, inviting the finger to be removed.
Figure 9:
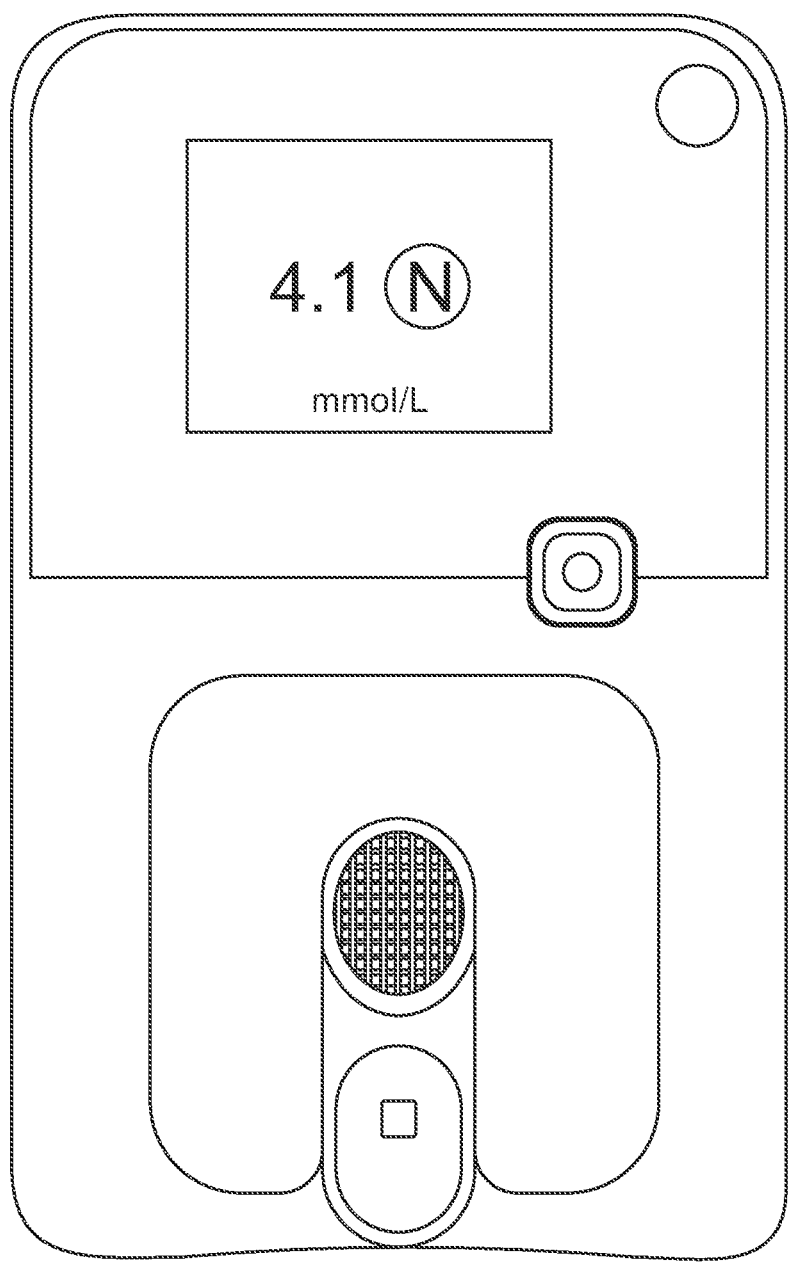
FIG. 9 shows a fourth stage of operation, presenting an indication of glucose level.

After the measuring process has completed, the visual display unit invites the subject to remove their finger, as illustrated in FIG. 8. After removal, the method continues with the step of allowing the elastomeric material to expand, thereby returning the intermediate circuit board to its original position.

FIG. 9

After analysing output data received during the scanning procedure, it is possible for the visual display unit 215 to provide an indication of glucose concentration. Furthermore, in addition to providing a numerical value, an indication may also be provided as to whether this concentration is considered to be low, normal or high. In an embodiment, for each of these possibilities, an appropriate colour is displayed. Thus, a low value may be presented in blue, a normal value in green and a high value in red.

It should be appreciated that similar graphical displays may be generated when detecting other blood-component levels.

The invention claimed is:

1. A pressure compensating non-invasive blood-component measuring apparatus, comprising:
    a plurality of electrically insulated substantially parallel electrodes mounted on a dielectric membrane;
    a main circuit board providing electrical connections to said electrodes, said main circuit board having a first orifice below said electrodes to allow flexing of said dielectric membrane;
    a housing for supporting said main circuit board, said housing having a second orifice to facilitate application of a finger onto said electrodes;
    a bottom circuit board supporting a force sensor;
    a plurality of fixing elements securing said bottom circuit board to said main circuit board, such that said bottom circuit board does not contact said housing directly; and
    an intermediate board that is guided but not restrained by said fixing elements, wherein said intermediate board is arranged to apply force onto said force sensor.

2. The apparatus of claim 1, wherein:
said fixing elements are metal rods, each metal rod of said metal rods having an upper end and a lower end;
said upper ends are secured to said main circuit board; and
said lower ends are secured to said bottom circuit board.

3. The apparatus of claim 1, wherein said intermediate board comprises an electrically conductive ground plane.

4. The apparatus of claim 1, further comprising a plastic support located between said dielectric membrane and said intermediate board.

5. The apparatus of claim 1, wherein an extending portion of said force sensor extends above a top surface of said bottom circuit board.

6. The apparatus of claim 5, wherein:
said extending portion comprises a metal ball; and
said metal ball contacts said intermediate board.

7. The apparatus of claim 5, wherein:
said extending portion is surrounded by an elastomeric material; and
said elastomeric material contacts said intermediate board.

8. The apparatus of claim 7, wherein said elastomeric material is a silicone rubber with a Shore durometer (type A) of less than forty.

9. The apparatus of claim 1, wherein:
said main circuit board supports control electronics for energizing and monitoring said electrodes to produce output data; and
operation of said control electronics is adjusted in response to pressure applied by said finger, as detected by said force sensor.

10. The apparatus of claim 9, wherein:
said main circuit board supports a visual display unit; and
said visual display unit is activated by said control electronics.

11. A method of measuring applied pressure, when a finger is pressed against a non-invasive blood-component detector, comprising the steps of:
engaging a finger against substantially parallel electrically insulated electrodes, wherein said electrodes are supported by a main circuit board having a first orifice and are exposed through a second orifice in a housing;
energizing and monitoring selected electrodes of said electrodes to produce output data; and
monitoring applied pressure using a force sensor supported by a bottom circuit board, wherein a plurality of fixing elements rigidly secure said bottom circuit board to said main circuit board, an intermediate board contacts said force sensor, and said intermediate board is guided but not restrained by said fixing elements.

12. The method of claim 11, further comprising the step of expanding an elastomeric material to return said intermediate board to an original position, after being displaced by an application of said pressure.

13. The method of claim 11, further comprising the step of measuring resistance of said force sensor to determine applied force, wherein increased applied force results in a higher measurable resistance.

14. The method of claim 11, further comprising the step of displaying a determination of glucose level on a visual display unit.

15. The method of claim 14, further comprising the step of displaying instructions to a user on said visual display unit.

* * * * *